(12) United States Patent
Lee et al.

(10) Patent No.: US 9,075,066 B2
(45) Date of Patent: Jul. 7, 2015

(54) CST1, DCC1, IFITM1 OR MELK AS MARKERS FOR DIAGNOSING STOMACH CANCER

(75) Inventors: Hee Gu Lee, Daejeon (KR); Eun Young Song, Daejeon (KR); Min Ah Kang, Gumi-si (KR); Jong Tae Kim, Daejeon (KR); Jae Wha Kim, Daejeon (KR); Young Il Yeom, Daejeon (KR); Seon Young Kim, Daejeon (KR); Kyung Chan Park, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 479 days.

(21) Appl. No.: 12/679,879

(22) PCT Filed: Apr. 21, 2009

(86) PCT No.: PCT/KR2009/002084
§ 371 (c)(1),
(2), (4) Date: Jan. 14, 2011

(87) PCT Pub. No.: WO2009/131365
PCT Pub. Date: Oct. 29, 2009

(65) Prior Publication Data
US 2011/0152106 A1 Jun. 23, 2011

(30) Foreign Application Priority Data

Apr. 21, 2008 (KR) .................. 10-2008-0036867
Apr. 21, 2008 (KR) .................. 10-2008-0036868
Apr. 21, 2008 (KR) .................. 10-2008-0036869
Apr. 21, 2008 (KR) .................. 10-2008-0036870

(51) Int. Cl.
*G01N 33/53* (2006.01)
*G01N 33/574* (2006.01)
*C12Q 1/68* (2006.01)

(52) U.S. Cl.
CPC ........ *G01N 33/57446* (2013.01); *C12Q 1/6886* (2013.01); *C12Q 2600/118* (2013.01); *C12Q 2600/136* (2013.01); *C12Q 2600/158* (2013.01); *G01N 2500/04* (2013.01)

(58) Field of Classification Search
USPC ............................................ 536/24.3, 24.33
See application file for complete search history.

(56) References Cited

U.S. PATENT DOCUMENTS

| 7,056,674 | B2 | 6/2006 | Baker et al. .................. 435/6 |
| 7,526,387 | B2 | 4/2009 | Baker et al. .................. 702/19 |
| 2005/0048542 | A1 | 3/2005 | Baker et al. .................. 435/6 |
| 2006/0204960 | A1* | 9/2006 | Nakamura et al. ............ 435/6 |
| 2006/0269921 | A1* | 11/2006 | Segara et al. ................. 435/6 |
| 2007/0184439 | A1 | 8/2007 | Guilford et al. |
| 2008/0293044 | A1* | 11/2008 | Kadyk et al. ................. 435/6 |
| 2009/0048266 | A1* | 2/2009 | Heise et al. ............ 514/253.07 |
| 2011/0104671 | A1* | 5/2011 | Dornan et al. ................ 435/6 |

FOREIGN PATENT DOCUMENTS

KR 1022040107145 A 12/2004
WO 2005/010213 2/2005

OTHER PUBLICATIONS

Gray et al (Cancer Research 2005 vol. 65: pp. 9751-9761, published online Nov. 1, 2005).*
Yang et al (Cancer Letters 2005 vol. 221: pp. 191-200).*
L'Esperance et al in Gene expression profiling of paired ovarian tumors obtained prior to and following adjuvant chemotherapy: Molecular signatures of chemoresistant tumors (International Journal of Oncology 2006, vol. 29: pp. 5-24).*
Chin et al., "High-resolution aCGH and expression profiling identifies a novel genomic subtype of ER negative breast cancer," *Genome Biology* 8:R215, 17 pp. 2007.
Gray et al., "Maternal Embryonic Leucine Zipper Kinase/Murine Protein Serine-Threonine Kinase 38 Is a Promising Therapeutic Target for Multiple Cancers" Cancer Res. 65(21): 9751-9761, Nov. 1, 2005.
Yang et al., "The interferon-inducible 9-27 gene modulates the susceptibility to natural killer cells and the invasiveness of gastric cancer cells" Cancer Letters 221: 191-200, 2005.

* cited by examiner

*Primary Examiner* — Catherine S Hibbert
(74) *Attorney, Agent, or Firm* — Seed IP law Group PLLC

(57) ABSTRACT

The present invention relates to a biomarker for gastric cancer, CST1 (cysteine proteinase inhibitor, type 2 family), DCC1 (Defective in sister chromatid cohesion homolog 1), IFITM1 (interferon induced transmembrane protein 1) or MELK (maternal embryonic leucine zipper kinase). More particularly, the present invention relates to a diagnostic composition for gastric cancer comprising an agent measuring the expression level of CST1, DCC1, IFITM1 or MELK, a kit comprising the composition, a method for detecting the marker, and a method for screening a therapeutic agent for gastric cancer using the marker.

2 Claims, 10 Drawing Sheets

| symbol | Chen | | | Boussioutas | | | | Hippo | | | Kim | | | Meta | |
|---|---|---|---|---|---|---|---|---|---|---|---|---|---|---|---|
| | Diffuse | Intestinal | Lymph | Mixed | Diffuse | Intestinal | Mixed | M | CG | Diffuse | Intestinal | Diffuse | Intestinal | Mixed | Diffuse | Intestinal |
| IFITM1 log2(FC) | 0.9857 | 1.1912 | 0.5716 | 1.0498 | 0.4311 | 0.5975 | 0.4891 | -0.3107 | -0.386 | 0.5608 | 0.4358 | 0.3851 | 0.1249 | 0.37 | 0.5907 | 0.5874 |
| p-value | 0.0003 | 3.08E-13 | 0.038 | 6.37E-05 | 0.1006 | 0.0451 | 0.2645 | 0.2174 | 0.1274 | 0.3548 | 0.1455 | | | | 0.022 | 1.26E-05 |
| q-value | 0.0037 | 1.57E-11 | 0.0952 | 0.0022 | 0.1887 | 0.0911 | 0.4442 | 0.4175 | 0.4453 | 0.5537 | 0.3128 | | | | 0.0728 | 7.65E-05 |

Differential expression between Diffuse and Intestinal Type    Download

| | Chen | Boussioutas | Hippo | Kim | Meta |
|---|---|---|---|---|---|
| IFITM1 log2(FC): DGC-IGC | -0.2056 | -0.1664 | 0.1249 | 0.2602 | 0.0033 |
| p-value | 0.3786 | 0.3978 | 0.8256 | 0.1044 | 0.2505 |
| q-value | 0.5733 | 0.6126 | 0.9707 | 0.492 | 0.557 |

Fig. 6

| symbol | Chen | | | | Boussioutas | | | | Hippo | | Kim | | | Meta | |
|---|---|---|---|---|---|---|---|---|---|---|---|---|---|---|---|
| | Diffuse | Intestinal | Lymph | Mixed | Diffuse | Intestinal | Mixed | M_CG | Diffuse | Intestinal | Diffuse | Intestinal | Mixed | Diffuse | Intestinal |
| MELK | | | | | | | | | | | | | | | |
| log2(FC) | 0.7985 | 1.433 | 1.496 | 1.0944 | | | | | 0.978 | 1.0265 | 0.2818 | 0.5111 | -1.0733 | 0.6861 | 0.9902 |
| p-value | 0.0001 | 3.70E-13 | 7.17E-08 | 8.77E-07 | | | | | 0.0044 | 0.0029 | | | | 0.0007 | 3.26E-08 |
| q-value | 0.0019 | 1.83E-11 | 4.85E-06 | 0.0001 | | | | | 0.1017 | 0.0246 | | | | 0.0139 | 6.71E-07 |

Differential expression between Diffuse and Intestinal Type                    Download

| | Chen | Boussioutas | Hippo | Kim | Meta |
|---|---|---|---|---|---|
| MELK | | | | | |
| log2(FC): DGC-IGC | -0.6345 | | -0.0485 | -0.2293 | -0.3041 |
| p-value | 0.0006 | | 0.7747 | 0.1887 | 0.01 |
| q-value | 0.0177 | | 0.905 | 0.6615 | 0.0997 |

Chen

| | Diffuse | Intestinal | Mixed |
|---|---|---|---|
| MELK | | | |

Boussioutas

| | Diffuse | Intestinal Metaplasia | Chronic Gastritis |
|---|---|---|---|
| MELK | | | |

Hippo

| | Diffuse | Intestinal | |
|---|---|---|---|
| MELK | | | |

Kim

| | Diffuse | Intestinal | Mixed |
|---|---|---|---|
| MELK | | | |

*Fig. 7*

| | colon cancer | stomach cancer | Breast cancer | Pancreatic cancer | Liver cancer |
|---|---|---|---|---|---|
| A. TargetID | | | | | |
| CST1 | | | | | |

| | colon cancer | stomach cancer | Breast cancer | Pancreatic cancer | Liver cancer |
|---|---|---|---|---|---|
| B. TargetID | | | | | |
| CST1 | | | | | |

| | colon cancer | stomach cancer | Breast cancer | Pancreatic cancer | Liver cancer |
|---|---|---|---|---|---|
| C. TargetID | | | | | |
| CST1 | | | | | |

| | colon cancer | stomach cancer | Breast cancer | Pancreatic cancer | Liver cancer |
|---|---|---|---|---|---|
| D. TargetID | | | | | |
| CST1 | | | | | |

*Fig. 8*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: CST1 primer

<400> SEQUENCE: 1
ccatggccca gtatctgagt                                               20

<210> SEQ ID NO 2
<211> LENGTH: 20
<212> TYPE: DNA
<213> ORGANISM: Artificial Sequence
<220> FEATURE:
<223> OTHER INFORMATION: CST1 primer

<400> SEQUENCE: 2
gaaggcacag gtgtccaagt                                               20

<210> SEQ ID NO 3
<211> LENGTH: 20
<212> TYPE: DNA
<213> ORGANISM: Artificial Sequence
<220> FEATURE:
<223> OTHER INFORMATION: DCC1 primer

<400> SEQUENCE: 3
gcagcacgaa tgctacttca                                               20

<210> SEQ ID NO 4
<211> LENGTH: 20
<212> TYPE: DNA
<213> ORGANISM: Artificial Sequence
<220> FEATURE:
<223> OTHER INFORMATION: DCC1 primer

<400> SEQUENCE: 4
cattttgcat cgaagaacga                                               20

<210> SEQ ID NO 5
<211> LENGTH: 20
<212> TYPE: DNA
<213> ORGANISM: Artificial Sequence
<220> FEATURE:
<223> OTHER INFORMATION: IFITM1 primer

<400> SEQUENCE: 5
atgtcgtctg gtccctgttc                                               20

<210> SEQ ID NO 6
<211> LENGTH: 20
<212> TYPE: DNA
<213> ORGANISM: Artificial Sequence
<220> FEATURE:
<223> OTHER INFORMATION: IFITM1 primer

<400> SEQUENCE: 6
tgtcacagag ccgaatacca                                               20

<210> SEQ ID NO 7
<211> LENGTH: 20
<212> TYPE: DNA
<213> ORGANISM: Artificial Sequence
```

```
<220> FEATURE:
<223> OTHER INFORMATION: MELK primer

<400> SEQUENCE: 7
tggctctctc ccagtagcat                                                 20

<210> SEQ ID NO 8
<211> LENGTH: 20
<212> TYPE: DNA
<213> ORGANISM: Artificial Sequence
<220> FEATURE:
<223> OTHER INFORMATION: MELK primer

<400> SEQUENCE: 8
atgcactggc ttgtccacag                                                 20
```

CST1, DCC1, IFITM1 OR MELK AS MARKERS FOR DIAGNOSING STOMACH CANCER

STATEMENT REGARDING SEQUENCE LISTING

The Sequence Listing associated with this application is provided in text format in lieu of a paper copy, and is hereby incorporated by reference into the specification. The name of the text file containing the Sequence Listing is 550077_401USPC_SEQUENCE_LISTING.txt. The text file is 2 KB, created on Feb. 22, 2011, and is being submitted electronically via EFS-Web.

TECHNICAL FIELD

The present invention relates to a specific biomarker for gastric cancer, CST1 (cysteine proteinase inhibitor, type 2 family), DCC1 (Defective in sister chromatid cohesion homolog 1), IFITM1 (interferon induced transmembrane protein 1) or MELK (maternal embryonic leucine zipper kinase). More particularly, the present invention relates to a diagnostic composition for gastric cancer comprising an agent measuring the expression level of CST1, DCC1, IFITM1 or MELK, a kit comprising the composition, a method for detecting the marker, and a method for screening a therapeutic agent for gastric cancer using the marker.

BACKGROUND ART

In 2005, a total of 65,479 persons died of cancer in Korea, accounting for 26.70 out of total deaths. 28.4 (21.1%) died of lung cancer, which is the leading cause of cancer-related death, 22.6 (16.8%) died of gastric cancer, 22.5 (16.7%) died of liver cancer, and 12.5 (9.3%) died of colon cancer per 100000 population. In spite of the decline in its mortality rate from 24% to 16% for the 10 years from 1996 to 2006, gastric cancer still remains one of the three leading causes of cancer death in Korea (see Table 1).

Mortality rate and Proportion of 10 Major Cancers in 2005

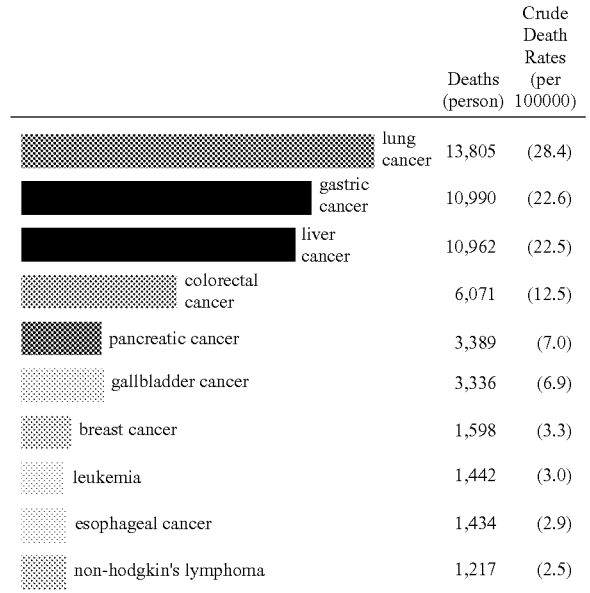

| | Deaths (person) | Crude Death Rates (per 100000) |
|---|---|---|
| lung cancer | 13,805 | (28.4) |
| gastric cancer | 10,990 | (22.6) |
| liver cancer | 10,962 | (22.5) |
| colorectal cancer | 6,071 | (12.5) |
| pancreatic cancer | 3,389 | (7.0) |
| gallbladder cancer | 3,336 | (6.9) |
| breast cancer | 1,598 | (3.3) |
| leukemia | 1,442 | (3.0) |
| esophageal cancer | 1,434 | (2.9) |
| non-hodgkin's lymphoma | 1,217 | (2.5) |

(source; National Statistical Office, 2005)

In addition, it is estimated that gastric cancer causes more than 16% of the male deaths in Korea or Japan. It is believed that a high incidence of gastric cancer in Asia including Korea and Japan is not due to race but due to differences in environmental factors which are strongly correlated with the occurrence of cancer, in particular, diet. The daily salt intake is known to be approximately 20 g in Korea, which are 2-fold higher than that in western countries. In particular, the high incidence of gastric cancer is reported in Korea, Japan, Finland, and Iceland, where salted fish is consumed. In addition, hereditary factors, as well as diet, have been suggested as a cause of gastric cancer. It appears that first-generation offspring of gastric cancer patients and people with blood type A are at increased risk of gastric cancer. Helicobacter Pylory (H.p) infection is one of the major risk factors for developing gastric cancer. The relationship between Helicobacter pyloric infection and gastric cancer has not been fully clarified yet, but Helicobacter pyloric infection is observed in 40-60% of Korean patients with digestive tract disorders or gastric cancer, indicating that individuals infected with *H. pylori* are at high risk of developing gastric cancer, compared with non-infected individuals. Therefore, eradication of *H. pylory* has been proposed for the prevention of gastritis and gastric cancer.

The underlying mechanism of cancer development remains poorly defined, but it is generally understood that cancer is the result of genetic events that disrupt the normal regulation of cell proliferation. Early gastric cancer is defined as tumor invasion confined to the mucosa, which has a considerably better prognosis. Thus, early diagnosis and treatment of gastric cancer contribute to the reduction of the mortality rate and cancer treatment cost.

Gastric cancer may exhibit with a wide range of symptoms from no symptoms to severe pain, and the symptoms are not marked characteristic symptoms, but overlap with the symptoms of various digestive illnesses. At an early stage, gastric cancer rarely causes symptoms, which if present, resemble typical digestive disorder or abdominal discomfort. Thus, people often ignore these symptoms, leading to an increase in the mortality rate.

To date, the diagnosis of gastric cancer has been made by physical examination. First, gastrointestinal X-ray examination methods may be broadly classified into the double contrast method, the compression method, the mucosal relief method, etc. Second, endoscopic examination is advantageous in that it directly visualizes the mucosa to find small lesions that are not detected by X-ray, and permits biopsy of suspicious lesions, whereby the diagnosis rate is increased. However, endoscopic examination has problems that there is a chance of contamination, and patients have to experience significant discomfort during the procedure.

In addition, surgical resection of the lesion is the most effective treatment for gastric cancer, and is the only curative treatment currently available for gastric cancer. Various methods can be employed in the surgical resection. For complete cure, surgical resection with a maximum surgical margin is generally recommended, but the extent of surgery may be determined in consideration of postoperative complications. At this time, other organs including nearby lymph nodes as well as the stomach are included in the surgical resection, and the extensive surgery may create a poor prognosis. Further, when gastric cancer spreads to other organs, radical surgery is not possible, and thus chemotherapy is adopted. Anticancer agents currently available serve to temporarily alleviate symptoms or to prevent recurrence and prolong survival time after surgical resection. However, chemotherapy causes severe side effects, and also imposes economic burden on the patients.

For the development of diagnostic agents for detecting the occurrence and development of gastric cancer and therapeutic agents as alternatives to solve the problems of surgical resection or chemotherapy, it is a prerequisite and an object of the present invention to screen biomarkers and to develop agents measuring the level of diagnostic marker.

On the other hand, human tumors express and secrete various specific molecules called cancer marker antigens. Currently, the sera of cancer patients are analyzed, and a variety of antigens have been provided for the diagnosis and treatment of cancer development and metastasis. As many as 60 tumor markers have been discovered thus far. Among them, some cancer markers are commercially applied, including AFP (hepatic cancer), CEA (colon, gastric, pancreatic, breast cancers), HCG (choriocarcinoma), PAP (prostate cancer), NSE (lung cancer), C15-3 (breast cancer), and CA19-9 (colon cancer, pancreatic cancer). Diagnostic markers or therapeutic agents which are highly useful in the diagnosis and treatment of gastric cancer, however, have not yet been developed.

DISCLOSURE

Technical Problem

Leading to the present invention, intensive and thorough research into gastric cancer-related genes, conducted by the present inventor, aiming to screen for differences in expression level between gastric cancer cells and colon, breast, and pancreatic cancer cells using a DNA chip, resulted in the finding that CST1, DCC1, IFITM1 and MELK are specifically up-regulated only in gastric cancer cells and has a possibility as a diagnostic marker for gastric cancer. It was also observed that early diagnosis of gastric cancer can be achieved by using the genes, and gastric cancer can be treated when the expression or secretion of the genes is suppressed.

Technical Solution

It is an object of the present invention to provide a diagnostic composition for gastric cancer, comprising an agent measuring the mRNA or protein level of CST1, DCC1, IFITM1 or MELK.

It is another object of the present invention to provide a diagnostic kit for gastric cancer, comprising the diagnostic composition for gastric cancer.

It is still another object of the present invention to provide a method for detecting the gastric cancer marker, CST1, DCC1, IFITM1 or MELK.

It is still another object of the present invention to provide a method for screening a therapeutic agent for gastric cancer using the gastric cancer marker, CST1, DCC1, IFITM1 or MELK.

Advantageous Effects

The present invention provides a diagnostic marker capable of detecting metastasis and prognosis of gastric cancer, and thus it is expected to provide useful information for the treatment and management of gastric cancer. The gastric cancer marker CST1, DCC1, IFITM1 or MELK according to the present invention allows the simple and accurate diagnosis of gastric cancer, and can be used as a specific target for the development of gastric cancer-specific anticancer agents, furthermore, in studies on tumorigenesis. Thus, it is expected to greatly contribute to early diagnosis of gastric cancer.

DESCRIPTION OF DRAWINGS

FIG. 6 is the result of data mining of the MELK gene;

FIG. 7 is the result of DNA chip data mining to compare expression levels of the same genes in gastric cancer, colon cancer, breast cancer, prostate cancer, and liver cancer (A, CST1; B, DCC1; C, IFITM1; D, MELK);

FIG. 8 is the result of electrophoresis to analyze the expression levels of the diagnostic marker, CST1, DCC1, IFITM1 and MELK genes in normal tissue and gastric cancer tissue by RT-PCR, in which odd numbered lanes represent the expression level of each gene in normal tissue, and even numbered lanes represent the expression level of each gene in cancer tissue (A, CST1; B, DCC1; C, IFITM1; D, MELK);

BEST MODE

Figure 1A:
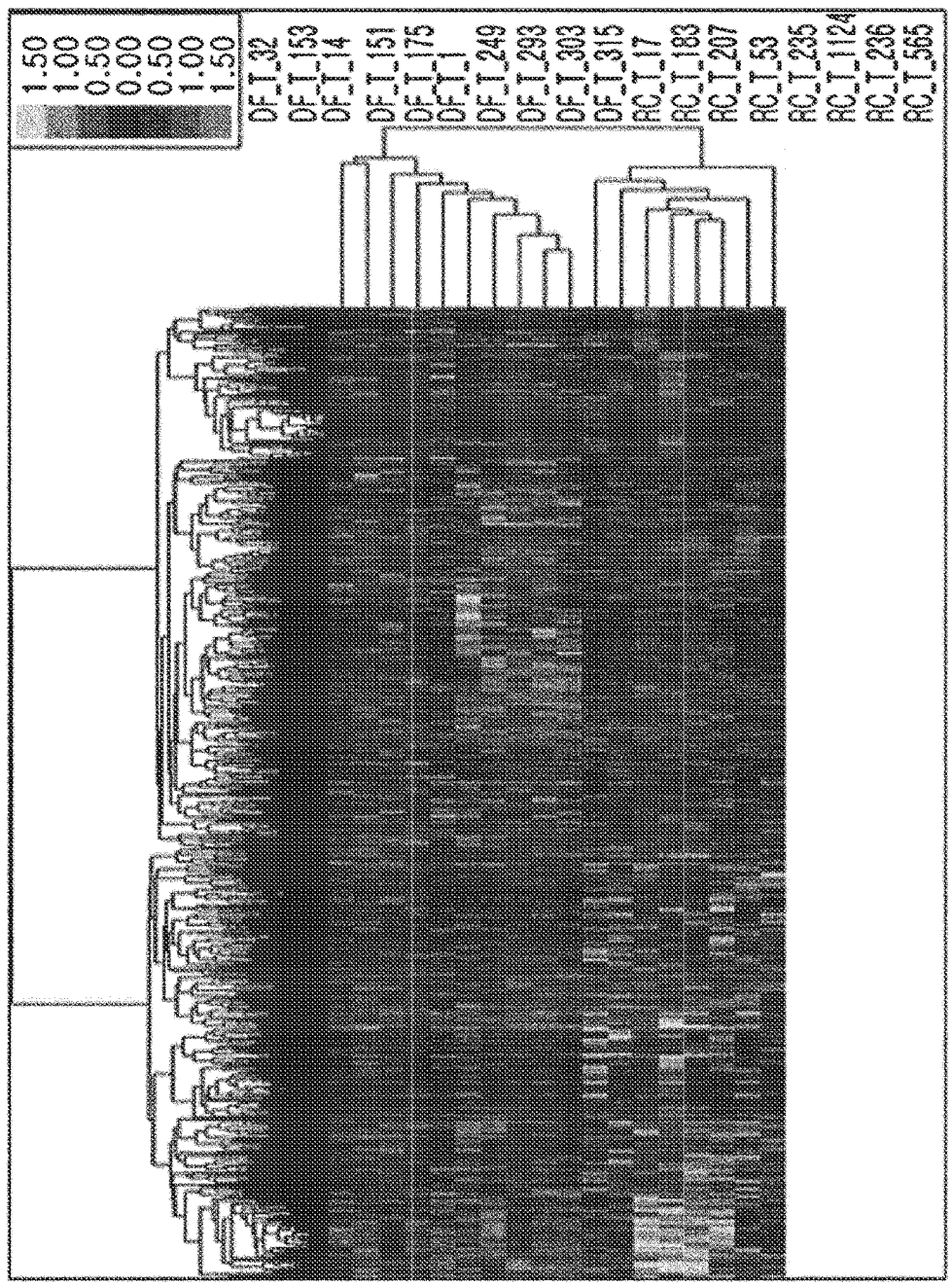
FIG. 1 (FIGS. 1A and 1B) is a result of microarray analysis by using human microarray chip (Illumina), which shows the gene expression levels in normal gastric tissue and gastric cancer tissue.

In accordance with an aspect to achieve the above objects, the present invention relates to a diagnostic composition for gastric cancer, comprising an agent measuring the expression level of CST1 (cysteine proteinase inhibitor, type 2 family), DCC1 (Defective in sister chromatid cohesion homolog 1), IFITM1 (interferon induced transmembrane protein 1) or MELK (maternal embryonic leucine zipper kinase).

The term "diagnosis", as used herein, refers to evaluation of the presence or properties of pathological states. With respect to the objects of the present invention, the diagnosis is to determine the incidence of gastric cancer.

The term "diagnostic marker, marker for diagnosis, or diagnosis marker", as used herein, is intended to indicate a substance capable of diagnosing gastric cancer by distinguishing gastric cancer cells from normal cells, and includes organic biomolecules, of which quantities are increased or decreased in gastric cancer cells relative to normal cells, such as polypeptides, nucleic acids (e.g., mRNA, etc.), lipids, glycolipids, glycoproteins, or sugars (e.g., monosaccharide, disaccharide, oligosaccharides, etc.). With respect to the objects of the present invention, the diagnostic marker for gastric cancer of the present invention is CST1, DCC1, IFITM1 or MELK gene and a protein encoded thereby, of which the expression is increased in gastric cancer cells as compared with the normal cells.

CST1 (cysteine proteinase inhibitor, type 2 family) is an extracellular secreted cystatin, and information on the gene and protein are available from NCBI (National Center for Biotechnology Information) (NM_001898, NP_001889). However, the relationship between function of CST1 and gastric cancer is still unclear.

DCC1 (Defective in sister chromatid cohesion homolog 1) is a protein that binds to the catalytic subunit of cyclin-dependent kinase, and is essential for biological function. Information on the gene and protein are available from NCBI (National Center for Biotechnology Information) (NM_024094, NP_076999). However, the relationship between function of DCC1 and gastric cancer is still unclear.

IFITM1 (interferon induced transmembrane protein 1) is a factor involved in the control of cell proliferation and differentiation, and is a multimeric complex involved in the transduction of anti-proliferation and cell adhesion signals. Information on the gene and protein are available from NCBI (National Center for Biotechnology Information) (NM_003641, NP_003632). However, the relationship between function of IFITM1 and gastric cancer is still unclear.

MELK (maternal embryonic leucine zipper kinase) is a protein serine/threonine kinase involved in stem cell renewal, cell cycle progression, and pre-mRNA splicing. Information on the gene and protein are available from NCBI (National Center for Biotechnology Information) (NM_014791, NP_055606). However, the relationship between function of MELK and gastric cancer is still unclear.

The present inventors have demonstrated that CST1, DCC1, IFITM1 or MELK can be used as a marker for diagnosing gastric cancer, as follows.

Figure 1B:
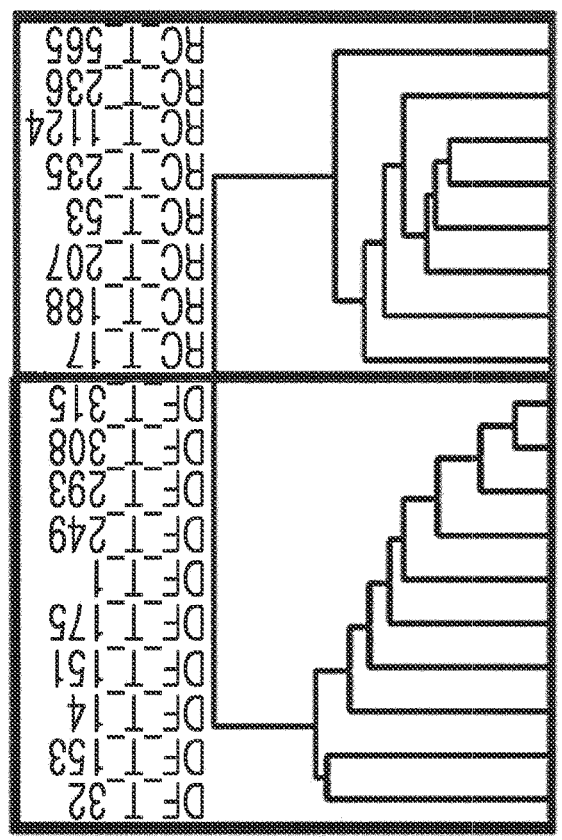
Figure 2:
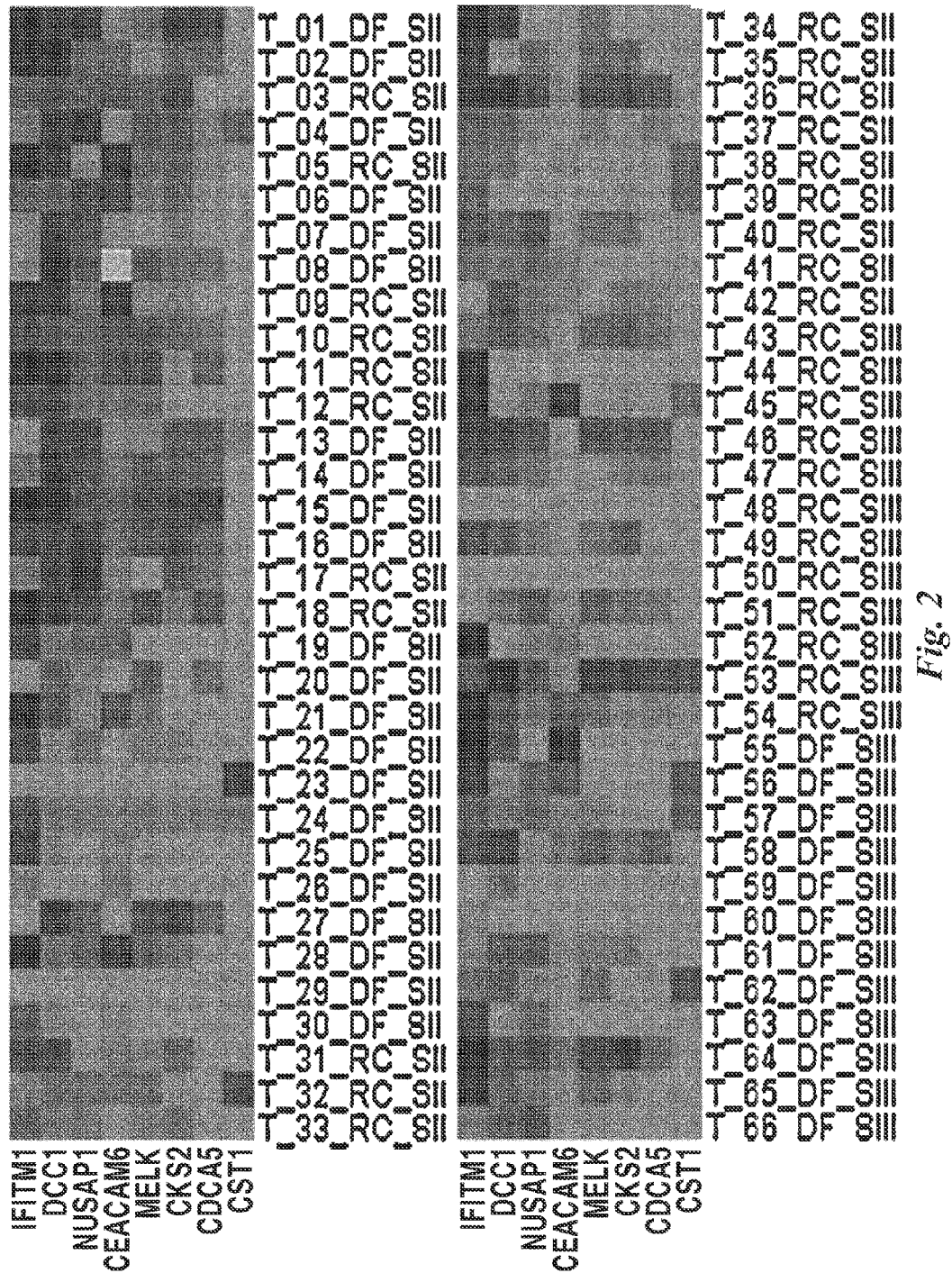
FIG. 2 is a graph showing genes that are specifically up-regulated in gastric cancer cell, based on the result of microarray analysis using 48K human microarray chip (Illumina)
Figure 3:
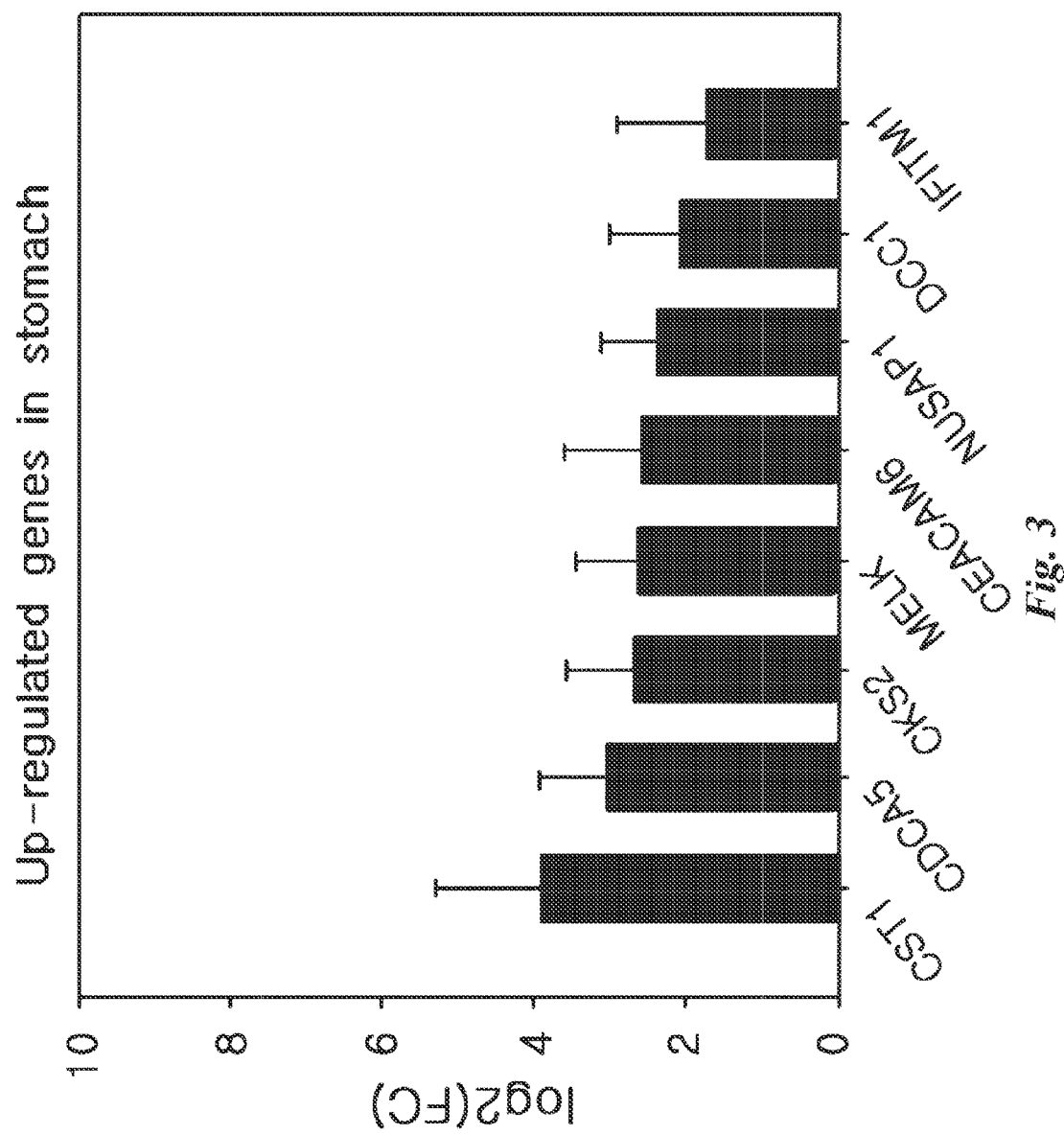
FIG. 3 is the result of data mining of the CST1 gene.
Figure 4:
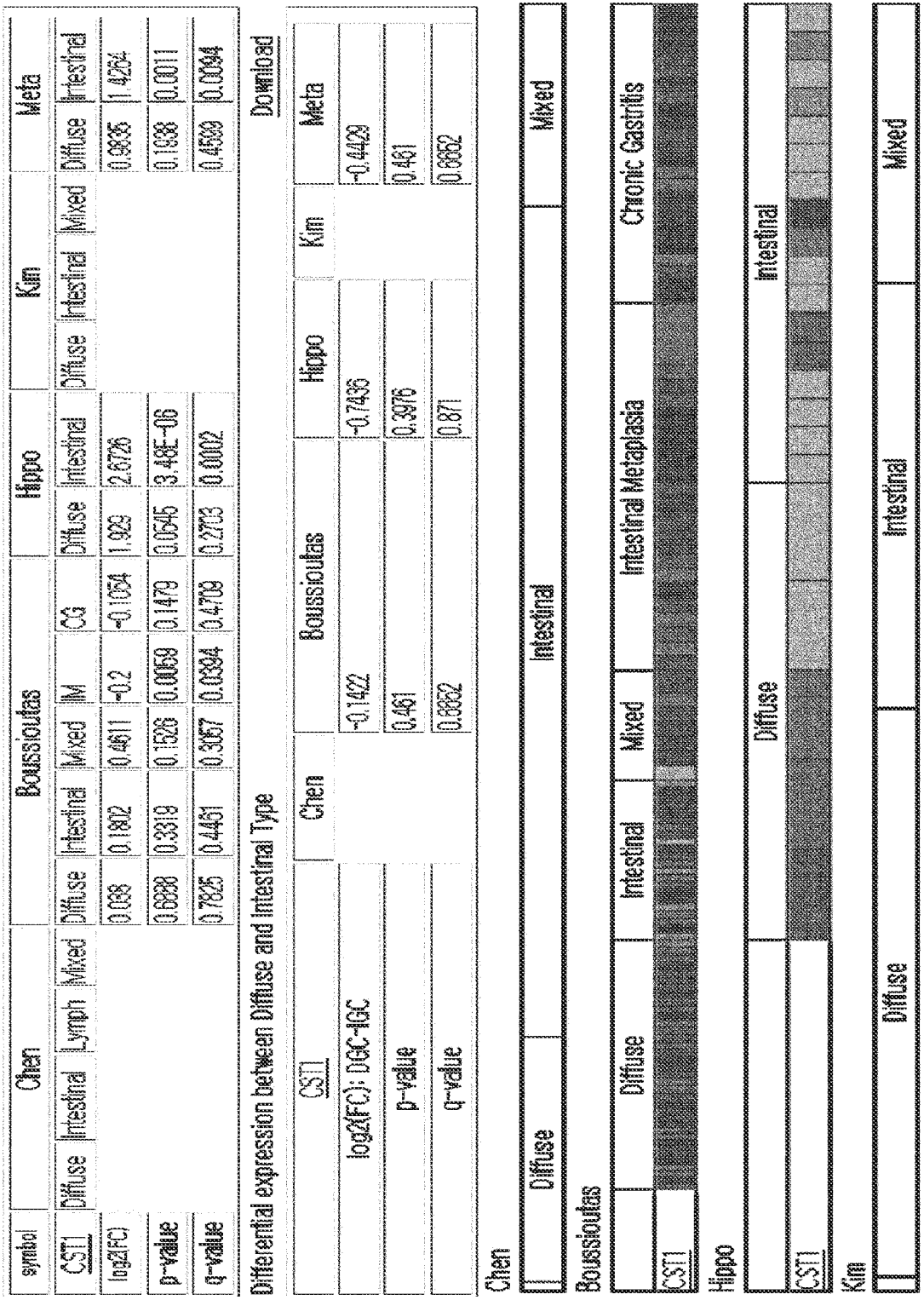
FIG. 4 is the result of data mining of the DCC1 gene.
Figure 5:
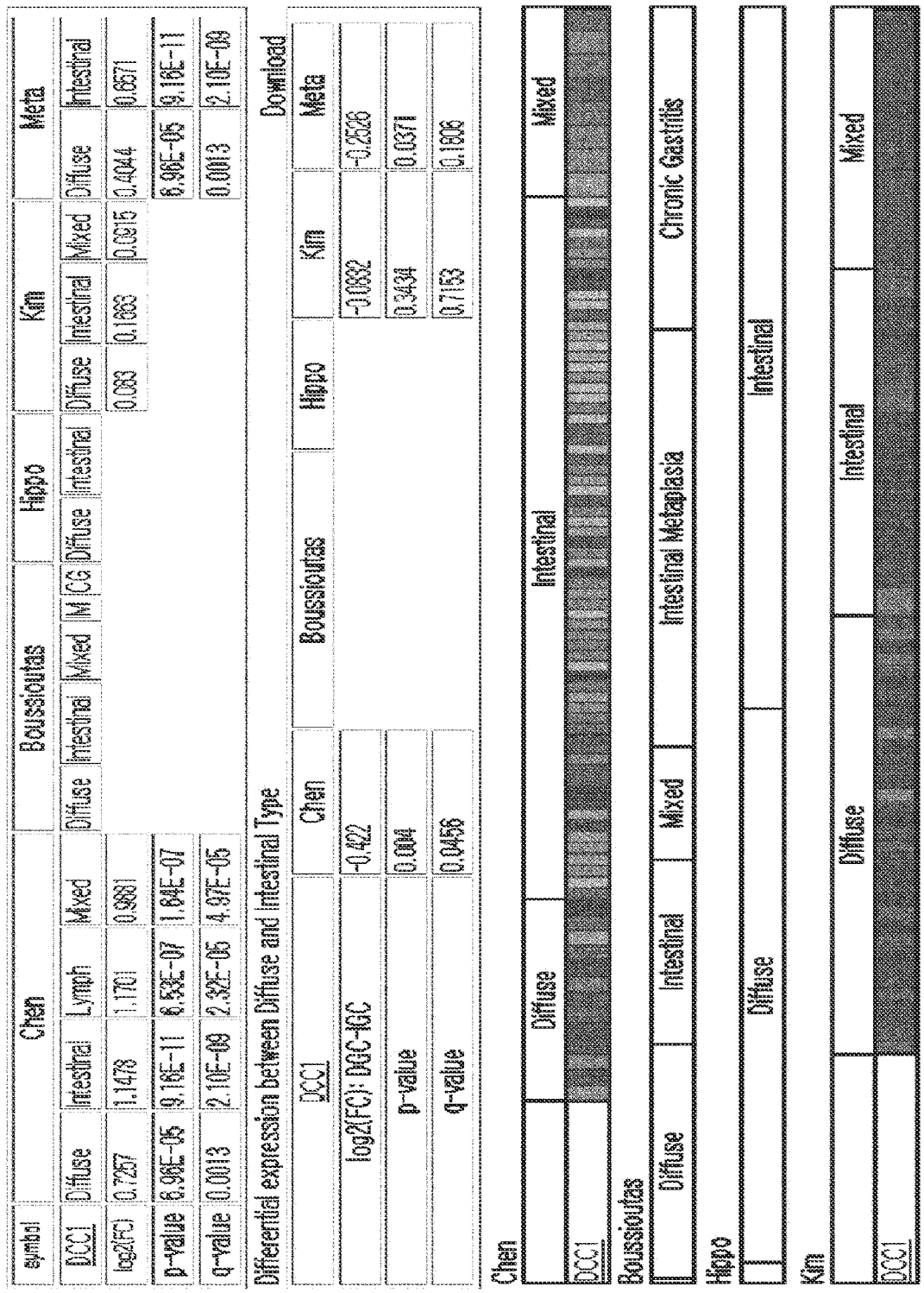
FIG. 5 is the result of data mining of the IFITM1 gene.

Specifically, expression patterns of 2,230 genes were analyzed using a DNA chip. 1,601 genes, which were not overexpressed in normal gastric epithelial cells but were prominently overexpressed in gastric cancer cells, were first obtained. They are divided into two clusters by clustering analysis (FIG. 1). Genes showing variances in expression level of 2-fold or more in 60% of patients were selected (FIG. 2). The expression levels of the same genes were also examined in colon cancer, breast cancer, and pancreatic cancer to finally screen the CST1, DCC1, IFITM1 or MELK gene that is specifically expressed in gastric cancer (FIGS. 3 to 6, and FIG. 7).

Figure 9:
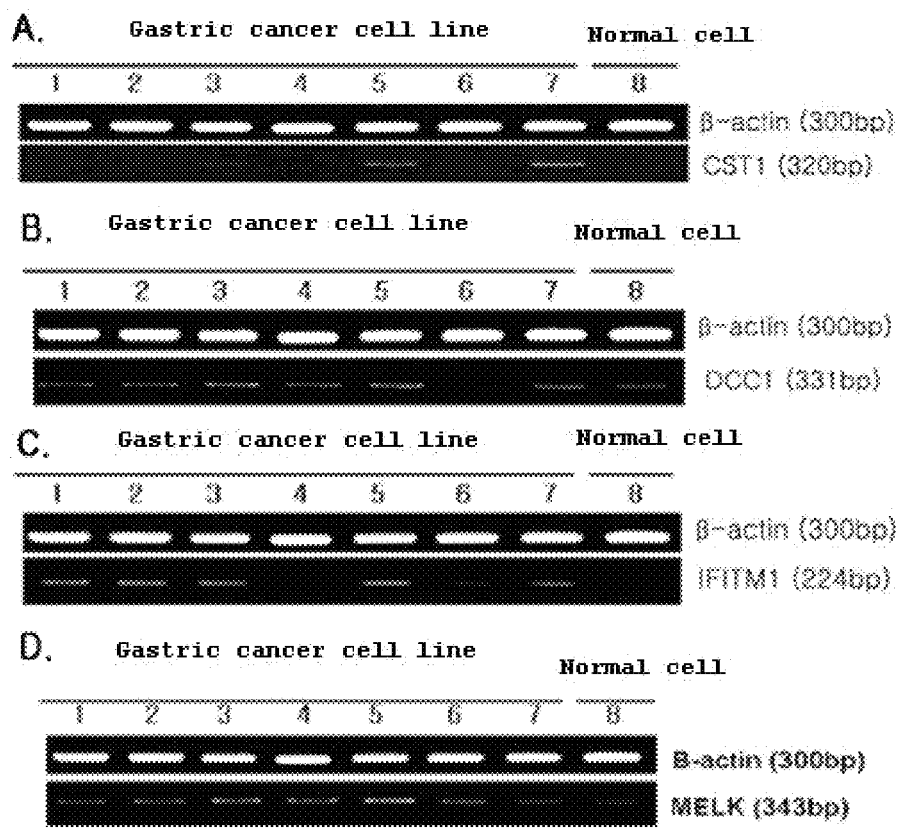
FIG. 9 is the RT-PCR result showing the expression levels of the marker genes for diagnosis of gastric cancer of the present invention in 7 types of gastric cancer cell lines (Lane 1, SNU1; Lane 2, SNU16; Lane 3, SNU216; Lane 4, SNU484; Lane 5, SNU620; Lane 6, SNU638; Lane 7, AGS) and in normal cell (Lane 8, Hs.683) (A, CST1; B, DCC1; C, IFITM1; D, MELK)

The selected CST1, DCC1, IFITM1 or MELK gene was subjected to RT-PCR using the primers prepared by the present inventors. A significant difference in the CST1, DCC1, IFITM1 or MELK expression levels between normal gastric tissues and gastric cancer tissues were observed (FIG. 8), and the difference in the CST1, DCC1, IFITM1 or MELK expression levels between normal cells and gastric cancer cell lines was also observed (FIG. 9).

The term "agent measuring the expression level of CST1, DCC1, IFITM1 or MELK", as used herein, means a molecule that is used for the detection of the marker CST1, DCC1, IFITM1 or MELK overexpressed in gastric cancer cells, preferably antibodies, primers, or probes being specific to the marker.

CST1, DCC1, IFITM1 or MELK expression level may be determined by measuring expression level of mRNA of CST1, DCC1, IFITM1 or MELK, or protein encoded thereby, and the expression level can be determined by measuring the expression level of a single gene or any one or more. The term "measurement of mRNA expression level", as used herein, is a process of assessing the presence and expression level of mRNA of the gastric cancer marker gene in biological samples for the diagnosis of gastric cancer, in which the amount of mRNA is measured. Analysis methods for measuring mRNA level include, but are not limited to, RT-PCR, competitive RT-PCR, real-time RT-PCR, RNase protection assay (RPA), Northern blotting and DNA chip assay.

The agent for measuring the mRNA level of the gene is preferably a pair of primers or a probe. Since the nucleotide sequence is readily found in NM_001898, NM_024094, NM_003641 and NM_014791 for the CST1, DCC1, IFITM1 and MELK genes, those who are skilled in the art can design primers or probes useful for specifically amplifying target regions of the genes, on the basis of the nucleotide sequence.

The term "primer", as used herein, means a short nucleic acid sequence having a free 3' hydroxyl group, which is able to form base-pairing interaction with a complementary template and serves as a starting point for replication of the template strand. A primer is able to initiate DNA synthesis in the presence of a reagent for polymerization (i.e., DNA polymerase or reverse transcriptase) and four different nucleoside triphosphates at suitable buffers and temperature. In the present invention, PCR amplification is performed using sense and antisense primers of CST1 polynucleotide, and the presence of the targeted product is examined to diagnose gastric cancer. PCR conditions and the length of sense and antisense primer can be modified on the basis of the methods known in the art.

The term "probe", as used herein, refers to a nucleic acid (e.g., DNA or RNA) fragment capable of specifically binding to mRNA, ranging in length from ones to hundreds of bases. The probe useful in the present invention is labeled so as to detect the presence or absence of a specific mRNA.

The probe may be in the form of oligonucleotides, single stranded DNA, double stranded DNA, or RNA. In the present invention, hybridization is performed using a probe complementary to CST1, DCC1, IFITM1 or MELK polynucleotide, and gastric cancer can be diagnosed by the hybridization result. Selection of suitable probe and hybridization conditions can be modified on the basis of the methods known in the art.

The primer or probe of the present invention may be chemically synthesized using a phosphoramidite solid support method or other widely known methods. These nucleic acid sequences may also be modified using many means known in the art. Non-limiting examples of such modifications include methylation, "capsulation", replacement of one or more native nucleotides with analogues thereof, and inter-nucleotide modifications, for example, modifications to uncharged conjugates (e.g., methyl phosphonate, phosphotriester, phosphoroamidate, carbamate, etc.) or charged conjugates (e.g., phosphorothioate, phosphorodithioate, etc.).

In accordance with a specific embodiment, the diagnostic composition for detecting the gastric cancer marker includes a pair of primers being specific to the CST1, DCC1, IFITM1 or MELK gene.

The "measurement of protein expression levels", as used herein, is a process of assessing the presence and expression levels of proteins expressed from gastric cancer marker genes in biological samples for diagnosing gastric cancer, in which the amount of protein products of the marker genes is measured using antibodies specifically binding to the proteins. Analysis methods for measuring protein levels include, but are not limited to, Western blotting, ELISA (enzyme linked immunosorbent assay), radioimmunoassay (RIA), radialimmunodiffusion, Ouchterlony immunodiffusion, rocket Immunoelectrophoresis, immunohistostaining, immunoprecipitation assay, complement fixation assay, Fluorescence Activated Cell Sorter (FACS), and protein chip assay.

A preferable agent for measuring protein level may be an antibody.

The term "antibody", as used herein, is a term known in the art, and refers to a specific protein molecule that indicates an antigenic region. With respect to the objects of the present invention, the antibody refers to an antibody that specifically binds to the marker of the present invention, CST1, DCC1, IFITM1 or MELK. To prepare the antibody, each gene is cloned into an expression vector according to the typical method, so as to obtain a protein encoded by the marker gene, and then the antibody may be prepared from the protein according to the typical method, in which a partial peptide prepared from the protein is included, and the partial peptide of the present invention includes at least 7 amino acids, preferably 9 amino acids, and more preferably 12 amino acids or more. There is no limitation in the form of the antibody of the present invention, and a polyclonal antibody, a monoclonal antibody, or a part thereof having antigen-binding property is also included, and all immunoglobulin antibodies are included. Furthermore, the antibody of the present invention also includes special antibodies, such as a humanized antibody.

The antibodies used in the detection of gastric cancer marker of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2, Fv or the like.

In accordance with another aspect, the present invention relates to a diagnostic kit for gastric cancer, comprising the diagnostic composition for gastric cancer.

The kit of the present invention can detect the marker by determining the mRNA or protein level of the diagnostic markers for gastric cancer, CST1, DCC1, IFITM1 or MELK. The detection kit of the present invention may comprise a primer to measure the expression level of the diagnostic marker for gastric cancer, a probe or an antibody selectively recognizing the marker, as well as one or more kinds of a composition, a solution, or an apparatus, which are suitable for the analysis method.

In a specific embodiment, the kit to measure a mRNA expression level of CST1, DCC1, IFITM1 or MELK may be a kit characterized by including essential elements required for performing RT-PCR. An RT-PCR kit may include test tubes or other suitable containers, reaction buffers (varying in pH and magnesium concentrations), deoxynucleotides (dNTPs), enzymes such as Taq-polymerase and reverse transcriptase, DNase, RNase inhibitor, DEPC water, and sterile water, in addition to a pair of primers specific for the marker gene. Also, the RT-PCR kit may include primers specific to a nucleic acid sequence of a control gene. Preferably, the kit of the present invention may be a diagnostic kit, characterized by including essential elements required for performing a DNA chip assay. A DNA chip kit may include a base plate, onto which cDNAs corresponding to genes or fragments thereof are attached, and reagents, agents, and enzymes for preparing fluorescent probes. Also, the base plate may include cDNA corresponding to a control gene or fragments thereof.

In another specific embodiment, the kit for measuring the protein level of CST1, DCC1, IFITM1 or MELK may include a matrix, a suitable buffer solution, a coloring enzyme, or a secondary antibody labeled with a fluorescent substance, a coloring substrate or the like for the immunological detection of antibody. As for the matrix, a nitrocellulose membrane, a 96 well plate made of polyvinyl resin, a 96 well plate made of polystyrene resin, and a slide glass may be used. As for the coloring enzyme, peroxidase and alkaline phosphatase may be used. As for the fluorescent substance, FITC and RITC may be used, and as for the coloring substrate solution, ABTS (2,2'-azino-bis (3-ethylbenzthiazoline-6-sulfonic acid)), OPD (o-phenylenediamine), or TMB (tetramethyl benzidine) may be used.

In accordance with still another aspect, the present invention relates to a method for detecting the gastric cancer marker CST1, DCC1, IFITM1 or MELK by comparing the expression level of CST1, DCC1, IFITM1 or MELK in the sample of a patient with that in normal cell in order to provide information needed for gastric cancer diagnosis.

More specifically, gene expression level can be detected at mRNA or protein level, and the isolation of mRNA or protein from a biological sample may be achieved using a known process.

The term "biological sample", as used herein includes samples displaying a difference in expression levels of a gastric cancer marker gene CST1, DCC1, IFITM1 or MELK, such as tissues, cells, whole blood, serum, plasma, saliva, sputum, cerebrospinal fluid or urine, but is not limited thereto.

With the detection methods, the occurrence of gastric cancer can be diagnosed by comparing the gene expression level in a patient with suspected gastric cancer to that in a normal control group. That is, the expression level of the marker of the present invention in suspected gastric cancer cell is compared to that in normal cell. If a significant increase in the expression level of the marker is observed in the suspected gastric cancer cell, the suspected gastric cancer can be diagnosed as gastric cancer.

Analysis methods for measuring mRNA levels include, but are not limited to, RT-PCR, competitive RT-PCR, real-time RT-PCR, RNase protection assay, Northern blotting and DNA chip assay. With the detection methods, the mRNA expression level in a patient with suspected gastric cancer is compared with that in a normal control, and the patient's suspected gastric cancer is diagnosed by determining whether expression levels of mRNA from the gastric cancer marker gene have significantly increased.

The mRNA expression levels are preferably measured by RT-PCR or DNA chip assay using primers being specific to the gene used as a gastric cancer marker.

RT-PCR products are electrophoresed, and patterns and thicknesses of bands are analyzed to determine the expression and levels of mRNA from a gene used as a diagnostic marker of gastric cancer while comparing the mRNA expression and levels with those of a control, thereby easily diagnosing the incidence of gastric cancer.

Alternatively, mRNA expression levels are measured using a DNA chip in which the gastric cancer marker genes or fragments thereof are anchored at high density to a glass-like base plate. A cDNA probe labeled with a fluorescent substance at its end or internal region is prepared using mRNA isolated from a sample, and is hybridized with the DNA chip, thereby diagnosing the incidence of gastric cancer.

Analysis methods for measuring protein levels include, but are not limited to, Western blotting, ELISA, radioimmunoassay, radialimmunodiffusion, Ouchterlony immunodiffusion, rocket immunoelectrophoresis, immunohistostaining, immunoprecipitation assay, complement fixation assay, FACS, and protein chip assay. With the analysis methods, a patient with suspected gastric cancer is compared with a normal control for the amount of formed antigen-antibody complexes, and the patient's suspected gastric cancer is diagnosed by evaluating a significant increase in expression levels of a protein from the gastric cancer marker gene.

The term "antigen-antibody complexes", as used herein, refers to binding products of a gastric cancer marker protein to an antibody specific thereto. The amount of formed antigen-antibody complexes may be quantitatively determined by measuring the signal intensity of a detection label.

Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescein, isothiocyanate, rhodamine, phycoerythrin, phycocyanin, allophycocyanin, o-phthaldehyde and fluorescamine. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Preferably, the protein expression levels are measured by ELISA. Examples of ELISA include direct ELISA using a labeled antibody recognizing an antigen immobilized on a solid support, indirect ELISA using a labeled antibody recognizing a capture antibody forming complexes with an antigen immobilized on a solid support, direct sandwich ELISA using another labeled antibody recognizing an antigen in an antigen-antibody complex immobilized on a solid support, and indirect sandwich ELISA, in which another labeled antibody recognizing an antigen in an antigen-antibody complex immobilized on a solid support is reacted, and then a secondary labeled antibody recognizing the another labeled antibody is used. More preferably, the protein expression levels are detected by sandwich ELISA, where a sample reacts with an antibody immobilized on a solid support, and the resulting antigen-antibody complexes are detected by adding a labeled antibody specific for the antigen, followed by enzymatic color development, or by adding a secondary labeled antibody specific to the antibody which recognizes the antigen of the antigen-antibody complex, followed by enzymatic development. The incidence of gastric cancer may be diagnosed by measuring the degree of complex formation of a gastric cancer marker protein and an antibody thereto.

Further, the protein expression levels are preferably measured by Western blotting using one or more antibodies to the gastric cancer markers. Total proteins are isolated from a sample, electrophoresed to be separated according to size, transferred onto a nitrocellulose membrane, and reacted with an antibody. The amount of proteins produced by gene expression is determined by measuring the amount of produced antigen-antibody complexes using a labeled antibody, thereby diagnosing the incidence of gastric cancer. The detection methods are composed of methods of assessing expression levels of marker genes in a control and cells in which gastric cancer occurs. mRNA or protein levels may be expressed as an absolute (e.g., μg/ml) or relative (e.g., relative intensity of signals) difference in the amount of marker proteins.

In addition, the protein expression levels are preferably measured by immunohistostaining using one or more antibodies against the gastric cancer markers. Normal gastric epithelial tissues and suspected gastric cancer tissues were collected and fixed, and then paraffin-embedded blocks were prepared according to a widely known method. The blocks were cut into small sections (several um in thickness), and attached to glass slides to be reacted with one or more selected from the antibodies according to a known method. Subsequently, the unreacted antibodies were washed, and the reacted antibodies were labeled with one selected from the above mentioned detection labels, and then observed under a microscope.

It is also preferable to analyze the protein level using a protein chip in which one or more antibodies against the gastric cancer marker are arranged and fixed at a high density at predetermined positions on a substrate. In this regard, proteins are separated from a sample and hybridized with a protein chip to form an antigen-antibody complex, which is then read to examine the presence or expression level of the protein of interest, thereby diagnosing the occurrence of gastric cancer.

In accordance with still another aspect, the present invention relates to a method for screening a therapeutic agent for gastric cancer, comprising the step of measuring the expression level of CST1, DCC1, IFITM1 or MELK gene or protein encoded by the gene after administration of a candidate substance that is expected to treat gastric cancer.

In detail, an increase or decrease in the CST1, DCC1, IFITM1 or MELK expression level is analyzed in the presence or absence of the candidate substance that is expected to treat gastric cancer, thereby effectively screening a therapeutic agent for gastric cancer. A substance that indirectly or directly decreases the CST1, DCC1, IFITM1 or MELK level can be selected as a therapeutic agent for gastric cancer. That is, the expression level of the marker CST1, DCC1, IFITM1 or MELK in gastric cancer cell is measured in the absence of a candidate substance, and then compared to that in the presence of the candidate substance. A substance that decreases the expression level of the marker of the present invention in its presence can be selected as a therapeutic agent for gastric cancer.

Mode for Invention

Hereinafter, a better understanding of the present invention may be obtained through the following examples which are set forth to illustrate, but are not to be construed as the limit of the present invention.

EXAMPLE 1

Detection of Up-regulated Genes in Gastric Cancer by Using DNA Chip

To select genes that are specifically up-regulated in gastric cancer cells than in normal gastric epithelial cells, a DNA chip (48K human microarray, Illumina) was used to analyze the expression levels of 2,230 genes.

First, total RNAs were extracted from the normal gastric epithelial and gastric cancer cells. Extraction of the total RNA was performed using an RNeasy Mini Kit (QIAGEN), and quantified using an Experion RNA StdSens (Bio-Rad) chip. The extracted total RNA was hybridized using the Illumina TotalPrep RNA Amplification Kit (Ambion). cDNA was prepared using a T7 Oligo(dT) primer, and in vitro transcription was performed using a biotin-UTP to prepare a biotin-labeled cRNA. The prepared cRNA was quantified using NanoDrop. cRNAs that were generated from the normal gastric epithelial and gastric cancer cells were hybridized to a Human-6 V2 (Illumina) chip. Then, to remove non-specific hybridization, the DNA chip was washed with an Illumina Gene Expression System Wash Buffer (Illumina), and the washed DNA chip was labeled with streptavidin-Cy3 (Amersham). The fluorescent-labeled DNA chip was scanned using a confocal laser scanner (Illumina), and fluorescent data present in each spot were saved with TIFF image files. TIFF image files were analyzed by Illumina BeadStudio version 3 (Illumina) to assess spot fluorescent intensities. Differences in spot intensities were normalized using 'quantile' with Avadis Prophetic version 3.3 program (Strand Genomics).

Gene expression patterns in normal gastric epithelial cells and gastric cancer cells were analyzed by the expression analysis of 1,601 genes that were obtained in the above procedure. At this time, hierarchical clustering analysis was employed, and the normal gastric epithelial cells and gastric cancer cells were found to be divided into two clusters (FIG. 1).

In addition, as compared to those in normal gastric epithelial cells, genes showing variances in expression level of 2-fold or more were observed in 60% of patients (FIG. 2), in which high and low expressions numbered 281 and 605, respectively. The expression levels of the same genes were also examined in colon cancer, breast cancer, and pancreatic cancer (FIG. 7) to finally screen the genes that are specifically expressed in gastric cancer (FIGS. 3 to 6). FIGS. 3 to 6 are the results of data mining to compare with various known microarray data.

EXAMPLE 2 mRNA Isolation from Tissue and Cell

For RT-PCR, normal gastric epithelial tissues and gastric cancer tissues were taken from 5 patients with gastric cancer, and mRNAs were isolated from the total 10 tissues. First, after surgical resection, the tissues were immediately washed with sterile phosphate buffered saline to remove blood, and then frozen in liquid nitrogen. Subsequently, total RNA was isolated by a guanidinium method, and single-step RNA isolation was performed. The isolated total RNA was quantified using a spectrophotometer, and then stored at a −70° C. freezer until use.

Total 7 gastric cell lines (SNU1, SNU16, SNU216, SNU484, SNU620, SNU638, AGS) were selected and obtained from Korean Cell Line Bank (KCLB: 28 Yongondong, Chongno-gu, Seoul, Korea). Each cell line was cultured in a suitable medium, DMEM (Invitrogen) or RPMI 1640 (Invitrogen) supplemented with 10% fetal bovine serum (FBS, Hyclon) and Penicillin/Streptomycin (1 mg/ml, Sigma) for 5-6 days, and then total RNA was isolated by a guanidinium method, as described above, to perform the single-step RNA isolation. The isolated RNA was quantified using a spectrophotometer, and then stored at a −70° C. freezer until use.

EXAMPLE 3

Comparison of Gene Expression by RT-PCR 4 genes were selected from the genes that were specifically up-regulated in gastric cancer, selected in Example 1, (data mining) and subjected to polymerase chain reaction. To construct primers, the entire DNA sequence of each gene was obtained from the NCBI CoreNucleotide ncbi.nlm.nih.gov, and primer sequence thereof was designed using a Primer3 program. Polymerase chain reaction was performed using the designed primer to examine the expression level of each gene (FIG. 8). The sequence of each primer is shown in Table 2.

TABLE 2

| | Name of oligo | Size of product (bp) | Sequence |
|---|---|---|---|
| 1 | CST1-<L> | 320 bp | CCA TGG CCC AGT ATC TCA GT |
| | CST1-<R> | | GAA GGC ACA GGT GTC CAA GT |
| 2 | DCC1-<L> | 331 bp | GCA GCA CGA ATG CTA CTT CA |
| | DCC1-<R> | | CAT TTT GCA TCG AAG AAC GA |
| 3 | IFITM1-<L> | 224 bp | ATG TCG TCT GGT CCC TGT TC |
| | IFITM1-<R> | | TGT CAC AGA GCC GAA TAC CA |
| 4 | MELK-<L> | 343 bp | TGG CTC TCT CCC AGT AGC AT |
| | MELK-<R> | | TAG CAC TGG CTT GTC CAC AG | cDNA for RT-PCR was constructed by reverse transcription using mRNA that was extracted from the tissues and cell lines in Example 2. The cDNA construction was performed using an AccuScript High Fidelity 1st Strand cDNA Synthesis Kit (STRATAGENE), and the resulting cDNA and primers in Table 2 were used for RT-PCR. As shown in FIG. 8, differences in the expression levels between normal and gastric cancer tissues were observed, and also observed in gastric cancer cell lines, as shown in FIG. 9.

EXAMPLE 4

Detection of CST1 and MELK Proteins by Immunohistochemical Staining

Immunohistochemical staining was conducted in order to examine the expression level of CST1 and MELK in gastric cancer tissues. Paraffin sections in which gastric cancer tissues taken from gastric cancer patients were embedded were deparaffinized with xylene and hydrated using graded alcohol washes. The hydrated sections were placed in 10 mM citric acid buffer (pH 6.0), and microwaved three times for 5 min.

Endogenous peroxidase was blocked by treatment with 3% hydrogen peroxide in methanol for 6 min. Thereafter, the sections were treated for 30 min with a working solution of a Vector kit (Cat No. PK 6102) so as to prevent non-specific protein binding. Incubation was carried out with a CST1 IgG antibody (Abcam, Cat No. ab26286) diluted in 1× PBS and a MELK IgG antibody (Abcam, Cat No. ab26286) diluted in 1× PBS at room temperature for 2 hrs and then with biotinylated anti-mouse Ig Ab (Vector kit) at room temperature for 30 min.

Figure 10:
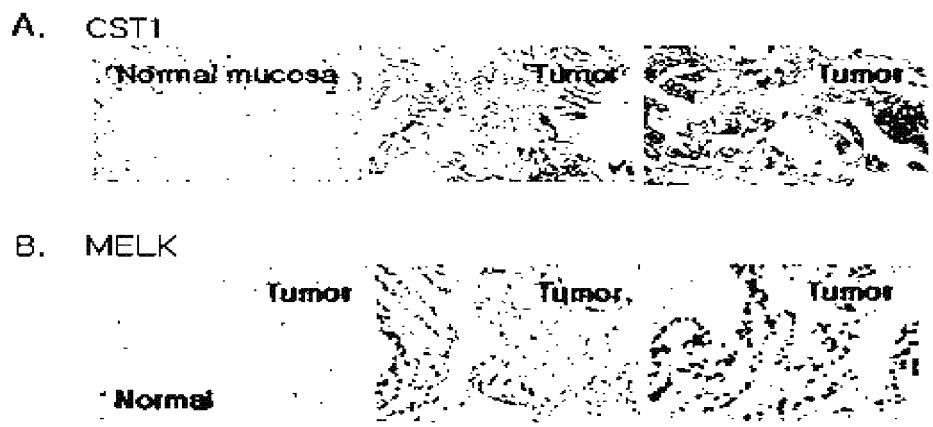
FIG. 10 is the result of immunohistochemistry using CST1 and MELK monoclonal antibodies, showing that the genes are specifically up-regulated in gastric cancer tissue having a high metastatic potential.

Afterwards, the sections were treated with an ABC Elite kit (Vector kit) at room temperature for 30 min and then reacted with a diaminobenzidine tetrahydrochloride substrate (Vector kit) for 2 min to analyze the expression levels of CST1 and MELK in gastric cancer tissues (FIG. 10).

The invention claimed is:

1. A method for diagnosing a gastric cancer in a subject, comprising the steps of measuring an expression level of a DCC1 gene in a biological sample from a patient with suspected gastric cancer by contacting the sample with primers having the nucleotide sequences set forth in SEQ ID NO:3 and SEQ ID NO:4; comparing the expression level of the DCC1 gene with a normal control sample expression level of the DCC1 gene; and diagnosing the patient with suspected gastric cancer as having gastric cancer when the expression level of the DCC1 gene in the biological sample from said patient is increased compared to the expression level of the DCC1 gene in the normal control sample.

2. The method according to claim 1, further comprising the steps of measuring an expression level of an IFITM1 gene in biological sample from a patient with suspected gastric cancer by contacting the sample with primers having the nucleotide sequences set forth in SEQ ID NO:5 and SEQ ID NO:6; comparing the expression level of the IFITM1 gene with a normal control sample expression level of the IFITM1 gene; and diagnosing the patient with suspected gastric cancer as having gastric cancer when the expression level of the IFITM1 gene in the biological sample from said patient is increased compared to the expression level of the IFITM1 gene in the normal control sample.

* * * * *

UNITED STATES PATENT AND TRADEMARK OFFICE
CERTIFICATE OF CORRECTION

PATENT NO. : 9,075,066 B2  
APPLICATION NO. : 12/679879  
DATED : July 7, 2015  
INVENTOR(S) : Hee Gu Lee et al.

Page 1 of 1

It is certified that error appears in the above-identified patent and that said Letters Patent is hereby corrected as shown below:

Title Page  
Item (56):  
"KR 1022040107145  A  12/2004" should read, --KR 1020040107145  A  12/2004--.

Signed and Sealed this  
First Day of March, 2016

Michelle K. Lee  
*Director of the United States Patent and Trademark Office*